United States Patent [19]

Dorn et al.

[11] Patent Number: 4,568,541

[45] Date of Patent: Feb. 4, 1986

[54] AGENTS WITH A HIGHLY PRONOUNCED RESIDUAL ACTION, FOR COMBATING ANIMAL ECTOPARASITES

[75] Inventors: Hubert Dorn; Wilhelm Stendel, both of Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 457,595

[22] Filed: Jan. 13, 1983

Related U.S. Application Data

[63] Continuation of Ser. No. 266,276, May 22, 1981, abandoned.

[30] Foreign Application Priority Data

Jun. 10, 1980 [DE] Fed. Rep. of Germany ....... 3021725

[51] Int. Cl.$^4$ ...................... A61K 31/78; A01N 25/00
[52] U.S. Cl. ..................................... 424/81; 514/781; 514/779; 514/944; 514/785; 514/778
[58] Field of Search ................................. 424/81, 362

[56] References Cited

U.S. PATENT DOCUMENTS

| | | | |
|---|---|---|---|
| 3,301,808 | 1/1967 | Mack et al. ........................ | 524/424 |
| 3,399,991 | 9/1968 | Littler ................................ | 424/362 |
| 3,959,237 | 5/1967 | Blank ................................. | 424/81 |
| 4,178,361 | 12/1979 | Cohen et al. ...................... | 424/22 |
| 4,183,950 | 1/1980 | Naumann et al. .................. | 424/306 |

FOREIGN PATENT DOCUMENTS

| | | |
|---|---|---|
| 2541087 | 9/1974 | Fed. Rep. of Germany ........ 424/81 |
| 1322805 | 7/1973 | United Kingdom . |
| 1427451 | 3/1976 | United Kingdom . |
| 1586258 | 3/1981 | United Kingdom . |

OTHER PUBLICATIONS

Ahrens et al., J. of Econom. Entomology, 70, 1977, pp. 581–585.

*Primary Examiner*—Delbert R. Phillips
*Assistant Examiner*—F. T. Moezie
*Attorney, Agent, or Firm*—Sprung, Horn, Kramer & Woods

[57] ABSTRACT

The invention relates to insecticidal formulations which have a pronounced residual action and contain (a) 0.1 to 20% by weight of an insecticidally active compound or compounds, (b) 1 to 40% by weight of a water-soluble gel-forming or lacquer-forming polymer, (c) 40 to 98% by weight of organic, water-miscible solvent, and (d) 0.1 to 10% by weight of one or more further additives.

4 Claims, No Drawings

AGENTS WITH A HIGHLY PRONOUNCED RESIDUAL ACTION, FOR COMBATING ANIMAL ECTOPARASITES

This is a continuation, of application Ser. No. 266,276, filed May 22, 1981, now abandoned.

The invention relates to new formulations with a highly pronounced residual action over a relatively long period, for combating animal ectoparasites, preferably for combating insects.

In the past, repeated attempts have already been made to extend the period of activity, that is to say to achieve a good residual action, of insecticidal substances, for example phosphoric acid ester compounds, by means of particular formulations. This has been effected and is effected, for example, by micro-encapsulating volatile insecticidal compounds. Incorporation of insecticides into polymers, from which they evaporate over a relatively long period, is carried out in practice, for example in the case of dog collars or fly strips using, for example, O,C-dimethyl O-(2,2-dichlorovinyl)phosphate as the active compound. Such processes have hitherto only seldom been used for combating animal ectoparasites, and especially insects, on large animals.

Thus, for example, insecticidal ear tags against ticks, which prefer the ear, have been tested. (See E. H. Ahrens et al., J. of Econom. Entomology, 70, 581–585).

Insecticidal tar formulations, which have a longer activity compared with the pure substance, have been tested against *Hydrotea irritans* in sheep (see R. N. Titchener, A. D. Herlyn and I. W. Newbold, Proceedings of the 8th Insecticide Conference 1975, 533–538).

Moreover, repellent formulations which are based on thermoplastic resins and prolong the repellent action when applied to the skin have been described (see British Patent Specification 1,322,805).

Insecticidal formulations based on N-vinyl-lactam polymers or vinyl acetate/crotonic acid copolymers for use on humans and animals are likewise described in the literature (see for example, U.S. Pat. No. 3,301,808 and British Patent Specification 1,427,451).

An insecticidal formulation which contains an added pressure-sensitive adhesive and is for use on animals has also been described (see DE-OS (German Published Specification) 2,658,725).

The process described in the DE-OS (German Published Specification) mentioned is directed towards combating symbovine flies, because this field of indication has recently achieved great significance, especially in the case of cattle. There are, above all, two reasons for this: (a) the adoption of new methods of mass raising of cattle (such as feed lots); and (b) the ban on the use of the substance DDT, which is highly effective against flies, in the case of animals which may be slaughtered.

Although a number of fly agents for large animals can at present be obtained, the provision of effective and, above all, permanent combating of symbovine flies in cattle was hitherto still an unsolved problem.

The reason may be found in the inadequate residual effect of the preparations which have hitherto been employed against symbovine flies. The problem of combating flies in cattle is thus less a problem of the active compound used than, rather, a problem of a suitable formulation with a long-term action. Similar problems arise with other large animals.

It should be possible to use a formulation with a long-term action both on wet animals and on dry animals. This is important that, in tropical countries, the cattle are usually dipped for combating ticks. After this dip, it would be advantageous also to provide the animals with additional protection against symbovine flies. On the other hand, it should also be possible to use such a formulation on dry animals.

However, the abovementioned insecticidal formulations for application to the hair coat can only be used on dry animals. The long-term action of these formulations is not sufficient.

Formulations with an insecticidal action and/or repellent action and which have an excellent residual action, which is also adequate for combating symbovine flies, and adhere to a wet or dry hair coat have now been found.

According to the present invention there are thus provided insecticidal formulations which have a pronounced residual action and can be applied both to wet animals and to dry animals, characterised in that it contains; (a) 0.1 to 20%, preferably 0.1 to 5%, by weight of an insecticidal active compound or compounds; (b) 1 to 40%, preferably 1 to 20% by weight of a water-soluble gel-forming or lacquer-forming polymer; (c) 40 to 98%, preferably 60 to 90%, by weight of an organic, water-miscible solvent, in which the said polymer does not dissolve; and (d) 0.1 to 10% by weight of one or more further additives, for example additive(s) selected from one or more of plasticisers, suspending auxiliaries, antioxidants and dyestuffs.

To prepare the formulation, polymers, or salts thereof, which are in themselves known are suspended in a solvent in which they are insoluble. On the other hand, the polymers swell in water to form a gel. The active compound is either suspended or dissolved in the solvent. The solvent must be water-miscible and must be able to evaporate more rapidly than water. The customary formulation auxiliaries can be added to the suspension in order to ensure that a suspension which can easily be shaken up or a homogeneous suspension is formed. It may also be desirable to add a plasticiser in order later to keep the film formed elastic.

If such a suspension is poured or sprayed onto a wet animal, the polymer swells as the solvent evaporates, and a gel is formed which dries out to a layer of lacquer or a film, thereby incorporating the active compound. This lacquer remains adhering to the hair coat for a long period and is only slowly—gradually—washed off by downpours of rain or a dip.

If the animal is dry or if, for example a stall wall is to be sprayed with the suspension, the following procedure is recommended:

The suspension is diluted with water in approximately equal proportions. It then still has a low viscosity (the polymer has not yet swollen), so that it can be applied without problems using the customary equipment. In this case also, a gel and later a film is formed after the solvent has evaporated, as already described above.

The following insecticides can preferably be used as the active compounds of component (a): a phosphoric acid ester insecticide (for example coumaphos, fenthion, trichlorofon, naled, bromophos, famphur, stirofos and diazinon), a carbamate insecticide (for example propoxur, crotenon and carbaryl), another chlorinated insecticidal compound (such as Toxaphene), and formamidine and or a derivative thereof (such as N-methyl-N'-2,4-xylol-N-(n-2,4-xylylforminidoyl)).

The groups of synthetic pyrethroids and insecticidal thioureas are also particularly suitable.

The activity of the insecticidal active compounds can be intensified by synergistic agents, such as piperonyl butoxide or sesamex.

Repellents can also be incorporated into these formulations, for example diethyltoluamide, dibutyl phthalate and 2-(octylthio)-ethanol.

It is also possible that "baits" are be added to the formulation together with insecticides. An increased number of symbovine flies are attracted to a treated animal and are killed on that animal, so that only part of the herd must be treated. Such baits are, for example: vanillin, (Z)-9-tricosenes, (Z)-8-dodecenyl-acetate, octyl butyrate and eugenol.

Possible gel-forming agents and film-forming agents of component (b) are, as stated, any macromolecular compounds which do not dissolve in the water-miscible, organic solvent and, after mixing with water, swell to form a gel which gives a type of film after drying.

If a classification of the macromolecular auxiliaries such as is described, for example, by Keipert et al. in Die Pharmazie 28, 145–183 (1973) is used, above all ionic macromolecules in salt form are employed. These are, inter alia, sodium carboxymethylcellulose, polyacrylic acid, polymethacrylic acid or a salt thereof, sodium amylopectin semiglycolate, alginic acid or propylene glycol alginate as the sodium salt, gum arabic, xanthan gum and guar gum.

Amphoteric macromolecule which fulfil the above requirements, such as protein derivatives, for example gelatins, are also suitable as components (b), as are non-ionic polymers, for example methylcellulose, other non-ionic cellulose derivatives and soluble starches.

Suitable solvents of component (c) are any of the water-miscible liquids which do not dissolve the macromolecule and evaporate more rapidly than water.

Possible solvents are, for example, alkanols (such as ethanol and isopropanol), ketones (such as acetone and methyl ethyl ketone) and glycol ethers (such as ethylene glycol monomethyl ether or monoethyl ether or the corresponding propylene glycol and derivatives).

One or more solvents can be used for the preparation of the pour-on formulations according to the invention.

Further auxiliaries of component (d) which are suitable are: (i) substances which can stabilise the suspension, for example colloidal silicic acid, montmorillonites and others; (ii) surface-active agents (includes emulsifiers and wetting agents), for example (1). anionic compounds, such as Na lauryl-sulphate, fatty alcohol ether-sulphates and the monoethanolamine salts of monoalkyl/dialkyl polyglycol ether orthophosphate; (2). cationic compounds, such as cetyltrimethylammonium chloride; (3). ampholytic compounds, such as di-Na N-lauryl-β-iminodipropionate or lecithin; and (4). non-ionic compounds, for example polyoxyethylated castor oil, polyoxyethylated sorbitane monooleate, sorbitane monostearate, cetyl alcohol, glycerol monostearate, polyoxyethylene stearate and alkylphenol polyglycol ethers; (iii) stabilisers for preventing the chemical degradation which occurs with some active compounds, such as antioxidants, for example tocopherols and butylhydroxyanisole; and (iv). plasticisers for elasticity of the film-forming agent, for example glycerol and propylene glycol.

The present invention also provides domesticated animals, characterised by being freed or protected from ectoparasiticidal insects by the external application to said animals of an insecticidal formulation of the present invention.

EXAMPLE 1

(Demonstration of the adhesion to the animal)

A formulation was prepared according to the following composition, using yellow iron oxide for colour-labelling: 10.0 g of Na alginate, 5.0 g of colloidal silicic acid, 2.0 g of yellow iron oxide pigment and isopropanol to 100 ml.

Two cattle were drenched completely. The above suspension was poured on in one case and sprayed on with a garden spray in the other case. After the animals had dried, a firmly adhering composition formed. The animals were now "showered" again with the hose for a prolonged period once daily. After 8 days, the adhering composition could still clearly be seen.

EXAMPLE 2

In a biological model experiment, the adhesion of a formulation according to the invention was tested in comparison with the adhesion of a conventional emulsion concentrate formulation.

In this experiment, the procedure was as follows: (the concentrates being diluted to the particular desired use concentration by adding water).

In each case 1 ml of the use concentration to be tested was pipetted onto a Petri dish ($\phi$10 cm) and distributed such that a thin film of liquid was formed. This film was then dried in air for 24 hours. After this period, in each case 2 Petri dishes per concentration with the dried-on film in the use concentration were left in this state until the start of the test. In each case 2 other Petri dishes per concentration, which likewise had been dried for a period of 24 hours, were then rinsed under a slow stream of running water for 15' or 60', and were then dried in air again for 24 hours.

Adult flies of the Stomoxys calcitrans species were then placed on the Petri dishes thus prepared with the use dilutions. The concentration at which the flies placed on the dishes were reliably killed within 5 minutes was established. If the concentration necessary for the destruction changed as a result of the rinsing-off, it was assumed that the active compound had been washed out of the film, whilst if the concentration necessary for the action remained constant, this proved that the active compound remained in the active compound film.

The results obtained for the comparison experiment can be seen from the following table:

The figures in the table give the concentration of active compound in ppm, which is necessary to destroy the flies (Stomoxys calcitrans) within 5 minutes.

| Petri dish with active compound film | conventional formulation | formulation according to the invention |
|---|---|---|
| dry | 1 | 30 |
| washing time 15' | 10 | 30 |
| washing time 60' | 1000 | 30 |

What is claimed is:

1. An insecticidal formulation which has a pronounced residual action and can be applied both to wet animals and to dry animals, containing (a) 0.1 to 20% by weight of a synthetic pyrethroid (b) 1 to 40% by weight of a water-soluble gel-forming or lacquer-forming polymer; (c) 40 to 98% by weight of an organic, water-miscible non-irritant solvent, in which the said polymer does not dissolve; and (d) 0.1 to 10% by weight of one or more further additives.

2. An insecticidal formulation according to claim 1, containing: (a) 0.1 to 5% by weight of the insecticidal active compound; (b) 1 to 20% by weight of the polymer; (c) 60 to 90% by weight of the organic, water-miscible solvent and (d) 0.1 to 10% by weight of the one or more further additives.

3. An insecticidal formulation according to claim 1 wherein the polymer of component (b) is sodium carboxymethylcellulose, polyacrylic acid, polymethacrylic acid or a salt thereof, sodium amylopectin semiglycolate, alginic acid or propylene glycol alginate as the sodium salt, gum arabic, xanthan gum, guar gum, a gelatin, methylcellulose, another non-ionic cellulose derivative or a soluble starch.

4. An insecticidal formulation according to claim 1, wherein the solvent of component (c) is an alkanol, ketone or glycol ether.

* * * * *